United States Patent [19]

Wilson et al.

[11] 4,005,527
[45] Feb. 1, 1977

[54] DEPTH GAUGE

[76] Inventors: Ralph S. Wilson, 2324 Ada Court, NE., Albuquerque, N. Mex. 87106; Charles E. Albright, 6629 Hensch NE., Albuquerque, N. Mex. 87109

[22] Filed: Dec. 22, 1975

[21] Appl. No.: 643,307

[52] U.S. Cl. .............................. 33/111; 33/169 B; 128/92 EB; 250/312
[51] Int. Cl.² ...................... G01B 3/04; G01B 3/28
[58] Field of Search ................ 33/111, 113, 169 B, 33/174 D; 128/2 A, 92 R, 92 EB; 250/312

[56] References Cited

UNITED STATES PATENTS

| | | | |
|---|---|---|---|
| 1,904,234 | 4/1933 | Hoskin et al. | 33/174 R |
| 2,187,039 | 1/1940 | Kohler | 33/111 X |
| 2,265,208 | 12/1941 | Thompson | 128/92 EB |
| 3,367,326 | 2/1968 | Frazier | 128/92 R |
| 3,915,162 | 10/1975 | Miller | 128/92 R |

OTHER PUBLICATIONS

The Journal of Bone and Joint Surgery, vol. XVIII, No. 1, Jan. 1936, pp. 134–139.

*Primary Examiner*—Charles E. Phillips
*Attorney, Agent, or Firm*—Richard A. Bachand

[57] ABSTRACT

A depth gauge includes a number of alternating sections of material which are X-ray transparent and X-ray opaque, respectively. The sections are carried in an elongated cylinder, and are each of a predetermined known length. The depth gauge is insertable into a hole or cavity to be measured, and viewed with X-ray techniques, from any angle. The number of sections of X-ray transparent and opaque material being within the hole, as seen by the X-ray techniques, indicate the depth into the hole which the pin is inserted. In one embodiment, a drill point is included on the end of the elongated cylinder to enable the depth gauge to be used additionally as a drill, so that depth to which the drill has cut can be monitored during the drilling process, if desired.

9 Claims, 5 Drawing Figures

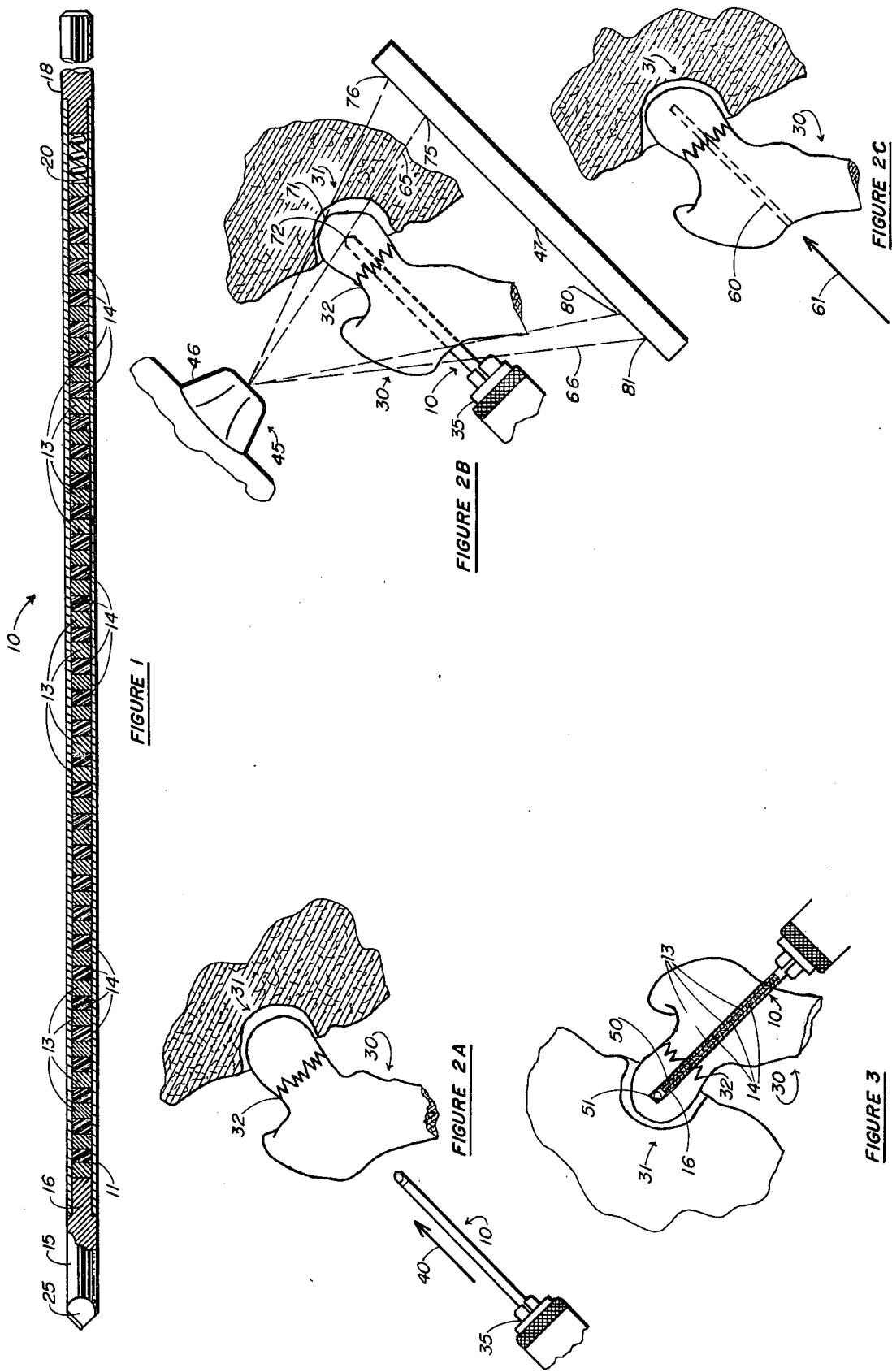

DEPTH GAUGE

BACKGROUND OF THE INVENTION

1. Field of the Invention

This invention relates to improvements in depth gauges and methods for using them, and, more particularly, to a depth gauge the scale of which is visible with X-rays and to a method for using same in surgical techniques.

2. DESCRIPTION OF THE PRIOR ART

Various types of depth gauges have been proposed for general use, and for surgical use in particular.

For example, in general, a depth gauge is shown by Kinney, U.S. Pat. No. 1,248,340, and includes an elongated rod onto which a scale or graduations are formed. A shoulder is carried on the rod and is movable along its axis. When the rod is inserted into a cavity or hole the depth of which is to be measured, and the shoulder brought to rest on the edges of the structure forming the hole, the depth of the hole can be readily measured or determined from the scale or graduations.

With respect to depth gauges for particular use in surgical environments, Biscow, U.S. Pat. No. 2,394,140, shows an obstetrical measuring instrument in which a scale is formed onto a finger of a flexible glove for directly measuring distances into cavities into which the fingers can be inserted.

Other surgical devices have been proposed for measuring various distances, such as surgical device described by Rubricuis, U.S. Pat. No. 3,740,779. This device is formed upon a surgical scalpel, and includes metered markings along its elongated axis for direct measurement, much like an ordinary ruler. At one end, a taper is formed for measuring circumferential diameters of an orifice, and, additionally, an arm is attached to the scalpel through a pivot pin to move out therefrom to serve as a caliper.

The instant invention, as will become apparent from the description below, has a principal use in performing orthopedic surgery of the type in which two or more sections of bone are immobilized by the insertion of a pin or wire therethrough. In this connection, the patent to Huene, U.S. Pat. No. 3,867,932, should be noted. This patent discloses a clamp assembly for immobilizing opposed segments of a fractured bone, and includes a drill which is used in conjunction with the clamp, operable to drill into the bone to a predetermined depth.

However, in the performing of most orthopedic surgical operations, especially those involving the hip bone, or other bones contained in a socket, the clamping device of Huene cannot be employed since the portion of the bone to which the clamp would otherwise be attached is inaccessible. Ordinarily, in such operations the surgeon performing the operation drills a hole into the two sections of the bone to be joined, exercising caution to insure that the drill bit does not penetrate beyond the end of the bone, for example, into the hip bone socket. The drill bit is then removed and a bone joining pin is then driven or inserted into the preformed hole. After the pin is in place, it is ordinarily cut where it protrudes adjacent the outer edge of the bone piece to be joined. This cut, however, often leaves exposed sharp edges upon the pin. After the operation is completed, these sharp edges, then deeply within the patient's body, are often a source of irritation to the patient upon movement of the limb into the bone of which the pin has been inserted.

To overcome this difficulty, it has been proposed that the bone joining pin to be inserted be precut so that its dimensions are precisely that desired to be employed in the bone joining operation. Thus, any sharp edges can be removed prior to the surgical procedure. However, since the dimensions of the pin needed are not known, due to many factors, such as the age of the patient, the location of the break in the bone, and so forth, a variety of pin lengths are required to be on hand prior to the commencement of the operation in readiness for use. This leaves the problem as to the choice of the pin of the appropriate length needed.

The difficulty in determining the precise depth of the hole which has been formed between the bones to be joined can be appreciated if one considers the inaccessibility of the area, for example, of the hip joint. If X-ray techniques are employed, care must be taken that the angle which the X-rays penetrate the pin receiving hole be precisely right angles so that its depth can be precisely measured, without being foreshortened by an angular perspective which would otherwise result. (Ordinarily, X-ray equipment is available, and, in fact, may be used during the drilling process to insure that the drill bit does not cut beyond the desired region and into the joint or socket.)

SUMMARY OF THE INVENTION

In light of the above, it is, therefore, an object of the invention to provide a depth gauge, the scale of which can be seen by X-ray techniques.

It is another object of the invention to provide an apparatus having alternating X-radiographically transparent and opaque portions which can be viewed from any angle for an indication of the depth to which it is inserted.

It is another object of the invention to provide an apparatus for measuring the depth of a hole formed into adjacent bone sections in surgical operations.

It is another object of the invention to provide a pin to be viewed with X-ray techniques to provide an indication of depth of its insertion.

It is still another object of the invention to provide a pin which can serve as a drill and as a means which can be viewed with X-ray techniques to determine the distance into a material into which it has been drilled.

It is a further object of the invention to provide a method for measuring the distance of a hole formed into adjoining bone sections in a surgical operation to facilitate subsequent insertion of a bone joining pin of proper length.

It is another object of the invention to provide an improved depth gauge which can be viewed with X-ray techniques without particular regard to the angle viewed.

It is still another object of the invention to provide a depth gauge having alternating X-ray opaque and X-ray transparent sections of predetermined length which can be seen with X-rays and counted to indicate the distance from its tip through its length of insertion.

It is another object of the invention to provide a method for measuring distances.

It is yet another object of the invention to provide a method for joining at least two pieces of bone material.

These and other objects, features and advantages will become apparent to those skilled in the art from the following detailed description when read in conjunction with the accompanying drawings and appended claims.

The invention, in its broad aspect, presents a depth gauge which includes a plurality of sections of material opaque to X-rays and a plurality of sections of material transparent to X-rays. The respective sections are alternately arranged, and each is of a known length dimension. When the depth gauge is inserted into an object to a depth to be measured, it can be viewed with X-ray techniques from any angle, whereupon the sections of material which are opaque to X-rays can be counted to indicate the depth into which the pin is inserted.

In one particular embodiment, a plurality of lead and plastic sections are enclosed within a sleeve. The sleeve is inserted into a hole or other receiving cavity, the depth of which is to be measured. The gauge is then viewed with X-ray techniques, from any angle, and the number of X-ray opaque sections, each of a predetermined length, are counted to indicate the depth into the object which the gauge has been inserted.

In another aspect of the invention, a method is presented for measuring holes preformed into a bone or sections of a bone during a surgical operation. The method includes the steps of inserting a pin having alternating X-ray opaque and X-ray transparent sections of a known length into the hole, and exposing the bone and pin to X-rays, from any angle. Then, the numbers of X-ray opaque and transparent sections within the bone are counted as disclosed by the X-rays.

In another aspect of the invention, a method for joining at least two pieces of bone material together includes drilling a hole extending into at least both of the two pieces of bone to be joined, inserting a depth gauge having alternating X-ray opaque and X-ray transparent sections of known length into the hole, and viewing the bone and the depth gauge with X-ray techniques. The number of X-ray opaque and X-ray transparent sections which are within the hole are than determined to indicate the depth of the hole within the bone. A bone joining pin is then selected having length corresponding to the length of numbers of the X-ray opaque and X-ray transparent sections, and the bone joining pin is inserted into the hole.

BRIEF DESCRIPTION OF THE DRAWING

The invention is illustrated in the accompanying drawing, wherein:

FIG. 1 is a plan view of a depth gauge, in cross section, embodying a drill bit, and including alternating X-ray transparent and X-ray opaque sections, in accordance with the invention.

FIG. 2A is a side view of a broken bone and the depth gauge of FIG. 1 carried in a drill in operative relationship thereto.

FIG. 2B is the broken bones of FIG. 2A, showing the depth gauge of FIG. 1 in its inserted position, and with X-ray equipment adjacent thereto.

FIG. 2C shows the broken bone sections of FIG. 2A, joined together with a pin inserted therebetween to immobilize them.

And FIG. 3 is a drawing depicting the broken bones of FIG. 2A, and the depth gauge of FIG. 1 in inserted position, as seen by X-ray techniques.

In the various figures of the drawing, like reference numerals are used to denote like parts. Various sizes and dimensions of the parts have been exaggerated or distorted in the drawing for clarity of illustration and ease of description.

DETAILED DESCRIPTION OF THE PREFERRED EMBODIMENTS

The depth gauge, in accordance with the invention, is shown in a cutaway plan view in FIG. 1, and is denoted generally by the reference numeral 10. The depth gauge 10 includes an elongated cylinder or sleeve 11. The sleeve 11 can be of any convenient material; however, since the depth gauge is intended for principal use in surgical operations, it is conveniently of stainless steel or the like.

A plurality of identical sections 13 are alternatingly interspaced with a corresponding plurality of sections 14 within the interior of the pin 11. The alternating sections 13 and 14, as will become apparent below, are viewed with X-radiographic techniques, and, serve to present indicia of the depth to which the pin is inserted into a hole or the like to be measured. The sections 13 and 14 are each of a known, predetermined length, for example, 0.125 inches, or other convenient length. Additionally, the sections 13 have a different X-ray transmitting coefficient than the sections 14. This X-ray transmission coefficient difference is referred to herein generally by denoting one of the plurality of sections, for example, the sections 13, as being X-ray opaque, and the other plurality of sections, such as the sections 14, being X-ray transparent. It is understood that the use of the terms X-ray transparent and X-ray opaque are in the relative sense only, with respect to each of the plurality of sections 13 or 14 compared to the other. It has been found, for example, that if one of the plurality of sections, such as the sections 13, is made of lead, and the other plurality of sections, such as the plurality 14 is made of a phenolic material or plastic, the difference in the X-ray opacity is apparent when viewed with typical X-radiographic techniques.

The pin 11 is enclosed at one end with a plug 16, and at the other end by a second plug 18, to maintain the positions of the respective sections 13 and 14. Additionally, a resilient spring means, such as the spring 20 is included within the pin 11 adjacent the enclosing plug 18. The spring 20 maintains the relative adjacent positions of the sections 13 and 14, and, additionally, presents a yielding means to absorb any expansion of the sections 13 and 14 within the pin 11 such as may be caused by temperature differences, and the like. Thus, expansions of the various sections 13 and 14 can occur without causing deformation in the pin 11 within which they are contained.

If desired, the enclosing plug 16 can include a drill bit 25 formed as a part thereof, to enable the entire depth gauge 10 to be used as a drill, the forward progress of which can be monitored with X-ray equipment, as will become apparent.

The depth gauge 10 can be employed in a surgical process in which at least two broken bone sections are desired to be interconnected with an immobilizing pin, a typically encountered surgical fact situation. Thus, as shown in FIG. 2A, a bone 30, broken near the socket 31 along a line 32 is drilled, as shown in the sequence of FIGS. 2A–2C. The drilling process is well known in the art, and is described herein only briefly for a full understanding of the invention. Usually, an ordinary drill bit is inserted in a drill 35, and is used to drill a hole through the two bone sections across the broken interface 32 to enable an immobilizing pin to be subsequently inserted thereinto. During the drilling process, extreme care must be taken to insure that the drill bit does not extend into the socket joint.

Thus, utilizing the depth gauge of FIG. 1 within the drill 35, as shown in FIG. 1, it is employed to drill in the direction of the arrow 40, as shown in FIG. 2A, until it is inserted to the desired depth, as shown in FIG. 2B. X-ray equipment 45 including an X-ray source 46 and X-ray detecting plate 47 is employed adjacent the broken bone 30 to monitor the progress of the drill bit/depth gauge 10. The depth is monitored as shown in FIG. 3, which illustrates the picture which is detected upon the X-ray receiving plate 47. Thus, the forward advance into the hole 50 formed by the drill bit into the bone 30 is monitored to insure that the foremost limit 51 does not extend into the socket region 31. Additionally, each of the plurality of X-ray opaque sections 13 and X-ray transparent sections 14 are also visible. Thus, the precise depth to which the drill has been inserted into the hole 50 can be readily determined merely by counting the number of the X-ray opaque sections 13 and the X-ray transparent sections 14 within the hole 50 from its point of entry 55, and multiplying that number by the known length of each of the sections, and adding the known length of the drill bit plug or tip 16. Thus, the depth of the drill cut is insured to be less than that which would otherwise extend into the socket region 31, and is precisely measurable in the same operation.

It should be specifically noted that the precise angle of the X-ray source 46 and X-ray receiving means 47, as shown in FIG. 2B, is relatively immaterial, since even if it were not set up at precisely a right angle to the drill or depth guage 10, the numbers of X-ray transparent and opaque sections, although they may appear foreshortened, nevertheless indicate by their numbers within the limits of the hole 50 between its point of entry 55 and terminal end 51 the depth or length of the hole 50.

Subsequently, in the operation, the drill bit depth guage 10 is removed from the bone 30, and a pin 60 driven or inserted thereinto, as shown in FIG. 2C, along the direction of the arrow 61, in a well known manner. Since the depth of the hole which has been drilled into the bone 30 is known, the length of the pin 60 to be inserted into the bone 30 can be determined prior to its insertion so that it can be chosen to be the proper length needed, and will not need to be cut or otherwise altered after insertion.

It should be pointed out that the X-ray source 46 is, in essence, a point source of X-rays. Thus, as can be seen in FIG. 2B, the shadow of the depth guage 10 is enlarged in its projection onto the X-ray receiving means 47, as denoted by the dotted lines 65 and 66. This enlarged projection eases the counting process, since the size of the individual opaque and transparent sections also appears enlarged.

Furthermore, various other distances which may be of interest to the surgeon can be readily calculated from the image on the X-ray receiving means 47. For example, if the distance from the point of entry of the depth guage 10 into the bone to the end of the bone 71 is desired to be calculated, it can be readily done as follows. The projection of the point 72 of furthest extension of the depth guage 10 into the bone can be seen on the X-ray receiving means 47 at a point 75. Likewise, the projection of the point 71 at the end of the bone 30 can be seen on the X-ray receiving means 47 at a point 76. The point 70 of entry of the depth guage 10 into the bone can be seen on the X-ray receiving means 47 at a point 80, and additional sections of the depth guage 10 will be visible on the X-ray receiving means 47 between the point 80 and a point 81 at which it is carried in the drill 35. Thus, the distance between the point 75 and 76 on the X-ray plate can be measured from point 80 in the direction of point 81. The number of alternating X-ray transparent and X-ray opaque sections represented on the X-ray receiving means 47 is then counted between point 75 and the measured distance from point 80, this then directly representing the distance between the point of the entry of the drill and the point 71 at the end of the bone 30.

It should be noted that although the depth guage 10 has been illustrated and described as being used in conjunction with or as a part of a drill bit, it need not necessarily be so fabricated. The drill bit point 25 can be eliminated from the structure, and the structure merely inserted into the hole to be measured, in accordance with the procedures outlined above.

Although the invention has been described and illustrated with a certain degree of particularity, it is understood that the present invention has been made only by way of example and that numerous changes in the combination and arrangement of parts may be resorted to without departing from the spirit and scope of the invention as hereinafter claimed.

We claim:
1. A gauge for measuring the depth of a hole, comprising:
    a plurality of elongated sections of material opaque to X-rays, each of known length dimension, and
    a plurality of elongated sections of material transparent to X-rays, each of known length dimension,
    said X-ray transparent sections being alternatingly carried with respect to said X-ray opaque sections, whereby when the depth gauge is inserted into the hole, the depth of which is to be measured, it can be viewed with X-ray techniques from any angle, the dimensions of the X-ray opaque sections and the X-ray transparent sections presenting an indication of the depth to which it is inserted by said X-ray opaque and transparent sections and further comprising an elongated sleeve into the interior of which said X-ray opaque sections and said X-ray transparent sections are implaced.
2. The depth gauge of claim 1 wherein said plurality of X-ray opaque sections are of lead, and said plurality of X-ray transparent sections are of plastic.
3. The apparatus of claim 1 wherein said X-rays opaque sections and said X-ray transparent sections are each of length of about 0.125 inch in length.
4. The depth gauge of claim 1 further comprising spring means contained within the interior of said sleeve to facilitate thermal expansion of said X-ray opaque sections and said X-ray transparent sections.
5. The depth gauge of claim 1 further comprising a drill point carried on said sleeve at one end thereof, whereby the depth gauge can drill to a desired depth, be X-rayed, and the depth determined.
6. A depth gauge for measuring distances of holes formed into bones in surgical operations, comprising:
    an elongated sleeve having an interior cavity formed axially therewithin;
    a plurality of sections of X-ray opaque material, and a plurality of sections of X-ray transparent material, alternatingly implaced within said interior cavity;

first means for enclosing said interior cavity at one end thereof;
second means for enclosing said interior cavity at another end; and
resilient spring means within said interior cavity adjacent an end thereof to facilitate thermal expansion of said X-ray opaque and said X-ray transparent sections without deformation of said sleeve;
said first enclosing means, said X-ray opaque sections, and said X-ray transparent sections all being of predetermined length, whereby when the pin is inserted into a hole preformed in a bone, and X-rayed from any angle, the distance which said gauge extends into the bone can be determined by the number of X-ray opaque and X-ray transparent sections disclosed by said X-ray to be within said bone.

7. The depth gauge of claim 6 wherein said X-ray opaque sections are of lead and said X-ray transparent sections are of plastic.

8. The depth gauge of claim 6 wherein said X-ray opaque sections and said X-ray transparent sections are each of length of about 0.125 inch.

9. The depth gauge of claim 6 wherein said first enclosing means comprises a drill point axially aligned with said sleeve to enable said sleeve to form a drill structure.

* * * * *